United States Patent [19]

Newman

[11] Patent Number: 4,648,513
[45] Date of Patent: Mar. 10, 1987

[54] PACKAGE AND DISPOSAL CONTAINER INCLUDING PLURAL TEAR PORTIONS

[75] Inventor: William R. Newman, Neenah, Wis.

[73] Assignee: Kimberly-Clark Corporation, Neenah, Wis.

[21] Appl. No.: 781,289

[22] Filed: Sep. 27, 1985

[51] Int. Cl.[4] ............................................. B65D 5/54
[52] U.S. Cl. .................................. 206/614; 206/610; 206/627; 229/40; 229/87 R; 604/385 R
[58] Field of Search ............................... 604/385, 385.1; 206/610, 614, 438, 830, 813, 627, 623, 632; 383/86, 37; 229/87.2, 87 A, 87 R, 40, 87 C

[56] References Cited

U.S. PATENT DOCUMENTS

| | | | |
|---|---|---|---|
| 1,476,267 | 12/1923 | Millholland | 206/830 X |
| 1,560,681 | 11/1925 | Fisher | 206/614 X |
| 1,803,348 | 5/1931 | Pasurka | 206/610 |
| 2,009,511 | 7/1935 | Nydegger | 229/87 R |
| 2,478,412 | 8/1949 | McMahan . | |
| 2,695,847 | 11/1954 | Fisher | 206/830 X |
| 2,750,033 | 6/1956 | Pickens . | |
| 2,855,884 | 10/1958 | Magill | 206/830 X |
| 3,035,379 | 5/1962 | Cloots . | |
| 3,035,578 | 5/1962 | Elinore | 604/385.1 |
| 3,136,104 | 6/1965 | Geer et al. . | |
| 3,193,181 | 7/1965 | Konjevich et al. . | |
| 3,276,670 | 10/1966 | Harvey . | |
| 3,420,433 | 1/1969 | Bostwick | 383/86 X |
| 3,469,769 | 9/1969 | Guenther | 383/37 X |
| 3,736,931 | 6/1973 | Glassman | 604/385 R |
| 3,856,142 | 12/1974 | Vessalo | 206/438 X |
| 3,973,567 | 8/1976 | Srinivasan et al. . | |
| 4,017,021 | 4/1977 | Crudgington | 229/87.2 |
| 4,053,046 | 10/1977 | Roark | 229/87 C |

FOREIGN PATENT DOCUMENTS

| | | | |
|---|---|---|---|
| 689964 | 7/1964 | Canada | 206/813 |
| 2494226 | 5/1982 | France . | |
| 25577 | of 1906 | United Kingdom | 604/385.1 |
| 2141396 | 12/1984 | United Kingdom . | |

Primary Examiner—William Price
Assistant Examiner—Bryon Gehman
Attorney, Agent, or Firm—P. A. Leipold; D. L. Traut; J. J. Duggan

[57] ABSTRACT

The invention is generally accomplished by providing a sheet of cover material, folding the sheet such that one portion to become the front extends up to a line slightly below the edge of the portion to become the back. The flap of the back portion extending above the front is coated with adhesive; the disposal container is formed by sealing the sides of the folded sheet. Outward of the seal lines that form the container are placed tear lines such as perforation lines. The object to be wrapped then is placed onto the exterior side of the front of the container, and the container is wrapped around the object and sealed with the adhesive strip on the flap to form a package. The ends of the package are then sealed. The package may be opened by tearing at the perforations and unrolling the container by releasing the adhesive flap to recover the wrapped article. After use the used article may be placed inside the container which is then sealed with the pressure-sensitive adhesive on the flap by adhering the flap to the front of the container.

In a particularly preferred form, the package is used for wrapping and disposal of catamenial devices. The packages may be made from continuous strips of polymer sheet that are heat sealed at the end of each package and then cut between the packages.

10 Claims, 14 Drawing Figures

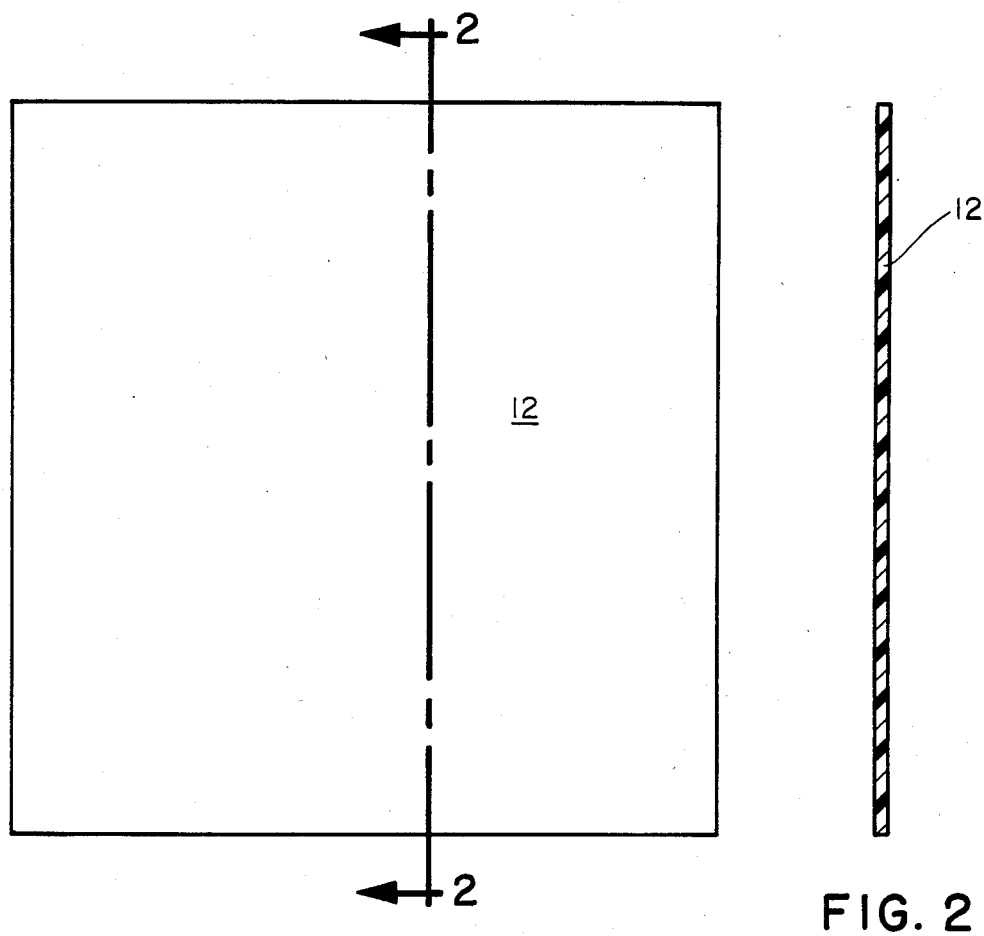
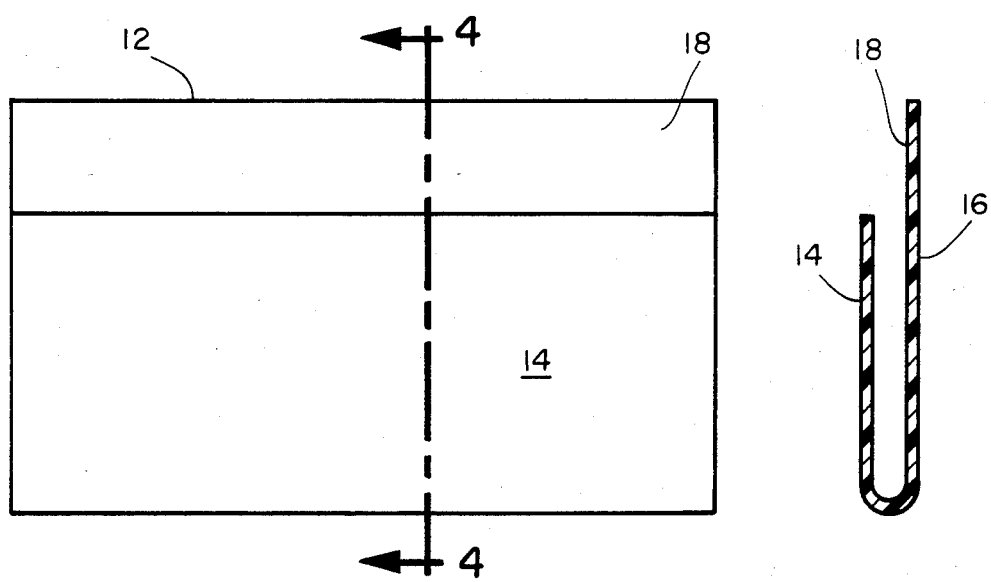

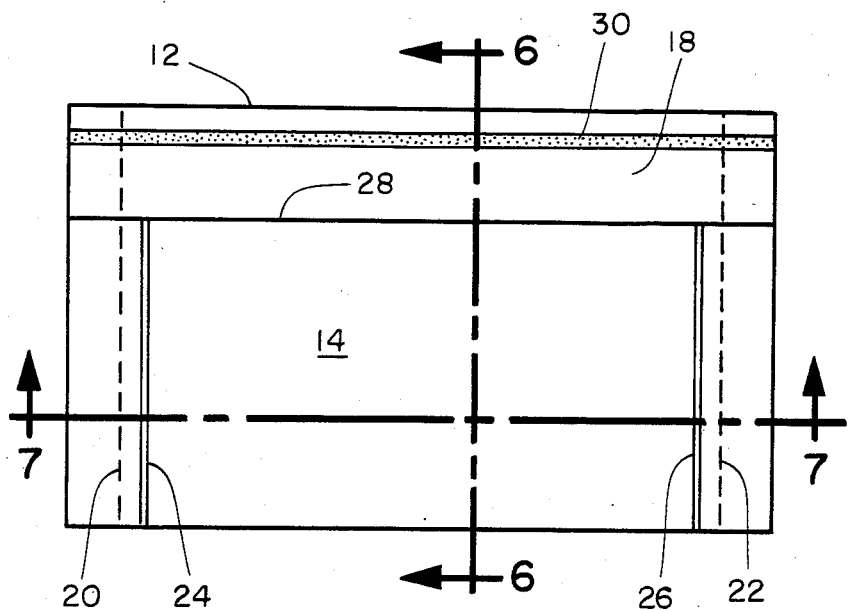
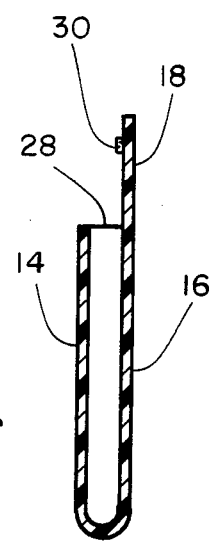
FIG. 5
FIG. 6
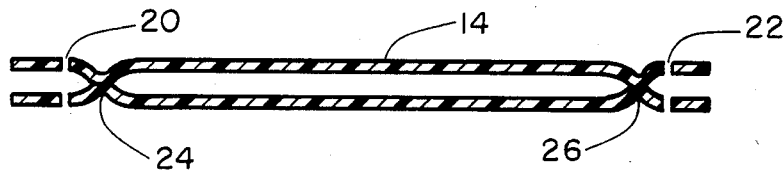
FIG. 7
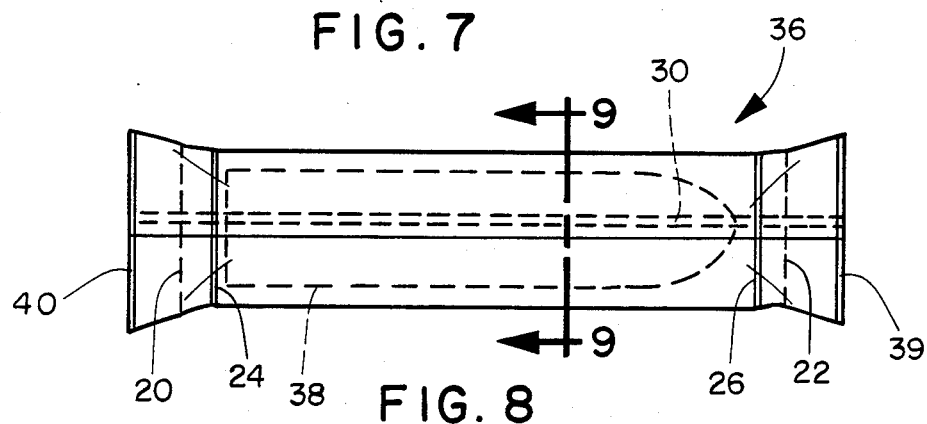
FIG. 8
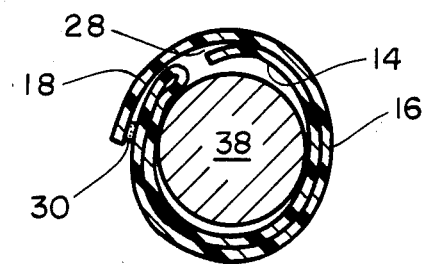
FIG. 9

PACKAGE AND DISPOSAL CONTAINER INCLUDING PLURAL TEAR PORTIONS

TECHNICAL FIELD

The present invention relates to improvements in packaging of sanitary items. It particularly relates to a method of packaging, dispensing and disposal of sanitary napkins.

BACKGROUND ART

The disposal problem in connection with catamenial appliances, disposable medical articles and the like is well known, but the present methods of disposal are not completely satisfactory. This is particularly so, since catamenial devices cannot be flushed down the toilet because of the resultant blockage of the plumbing. Nevertheless, a napkin has an odor and an undesirable appearance and complete concealment and protection against these odors and appearance is of primary importance. Further, it is important that the method of protection be convenient and low cost.

This problem is particularly acute in public rest rooms where traffic may be heavy and a rather large number of napkins require disposal, and particularly in public rest rooms where people tend to become careless and either flush the napkin down the toilet or exercise insufficient care in disposal because of the inconvenience. Such facilities are usually equipped with a receptacle that has a closed door which seals rather tightly and this assists in retention of odors therein.

In a typical disposal, the napkin is usually removed and folded in face-to-face relation to retain the soiled surface sandwiched within, and an additional piece of paper or the like is frequently wrapped around the outside. When such disposal is effected, the rest room is retained clean and offensive odors are minimized. However, this requires an exercise of care by the person involved which is often not in fact performed. In addition, there is an additional disposal problem by the janitor who must service these containers and once again expose the napkins to the atmosphere where the odors become a problem. Moreover, the articles often continue in open view when they are hauled away to an incinerator or the like.

In the formation of disposal catamenial devices and other disposable articles, it is necessary that the package not be so complicated or expensive that it adds significantly to the cost of the article. Further, any disposal means to be used must be convenient to the consumer, both to carry and use.

U.S. Pat. No. 2,750,033-Pickens, discloses a feminine napkin that is packaged in an envelope. The envelope is designed such that it also may be used for disposal of the used napkin. U.S. Pat. No. 3,973,567-Srinivasan et al., provides a package that also may be used for disposal of the catamenial device after use. Srinivasan et al. provides a wrapping that is a sheet that is held in place by the adhesive element of the feminine napkin and then after use may be again wrapped around the napkin and held by the adhesive of the napkin.

There remains a need for low-cost, effective system for packaging and sealing catamenial devices for disposal after use.

DISCLOSURE OF THE INVENTION

It is an object of this invention to overcome disadvantages of prior inventions.

It is an additional object of this invention to provide a low-cost package that can also serve as a disposal container for a disposable device.

Another object of this invention is to provide a packaging for a catamenial device that is discreet, sanitary and provides its own disposal container for used devices. A further object of this invention is to provide a low-cost method for continuously packing and sealing disposable articles.

These and other objects of the invention are generally accomplished by providing a sheet of cover material, folding the sheet such that one portion to become the front extends up to a line slightly below the edge of the portion to become the back. The flap of the back portion extending above the front is coated with adhesive; the disposal container is formed by sealing the sides of the folded sheet. Exterior of the seal lines that form the container are placed tear lines such as perforation lines. The object to be wrapped then is placed onto the exterior side of the front of the container, and the container is wrapped around the object and sealed with the adhesive strip on the flap to form a package. The ends of the package are then sealed. The package may be opened by tearing at the perforations and unrolling the container by releasing the adhesive flap to recover the wrapped article. After use the used article may be placed inside the container which is then sealed with the pressure-sensitive adhesive on the flap by adhering the flap to the front of the container.

In a particularly preferred form the package is used for wrapping and disposal of catamenial devices. Yet further, the preferred form may be made in continuous strips of polymer sheet that are heat sealed at the end of each package and then cut between the packages.

BRIEF DESCRIPTION OF THE DRAWINGS

FIG. 1 is a plan view of a sheet suitable for use in forming the package of the invention.

FIG. 2 is a cross section on line 2—2 of FIG. 1.

FIG. 3 is a plan view of a folded sheet folded in accordance with the formation of the package of the invention.

FIG. 4 is a cross-sectional view of line 4—4 of FIG. 3.

FIG. 5 is a view of the folded sheet of FIG. 3 to which has been added perforation lines and sealing lines.

FIG. 6 is a cross-sectional view of line 6—6 of FIG. 5.

FIG. 7 is a cross-sectional view along cross-sectional line 7—7 of FIG. 5.

FIG. 8 is a view of a package of the invention.

FIG. 9 is a cross-sectional view of FIG. 8 on line 9—9 of FIG. 8.

MODES FOR CARRYING OUT THE INVENTION

The invention has numerous advantages over the prior practices. The instant invention allows the same material to be used both for a secure discreet package and for disposal. The package is low in cost and is easily, continuously formed. The package of the invention allows sanitary storage of the disposable article prior to use and provides a readily available and discreet disposal container that will prevent the spread of odors. These and other inventions will become apparent from the detailed description of the invention below.

FIG. 1 illustrates a sheet 12 suitable for formation of the package of the invention. The sheet may be of any material. However, a polymer sheet of a material such as polypropylene or polyethylene is generally preferred as it is heat sealable, resistant to transmission of water and odor and low in cost. FIG. 2 is a cross section of the sheet 12 of FIG. 1.

FIGS. 3 and 4 illustrate the sheet 12 that has now been folded such that is has a front portion 14, back portion 16 and flap 18.

Figure 10:
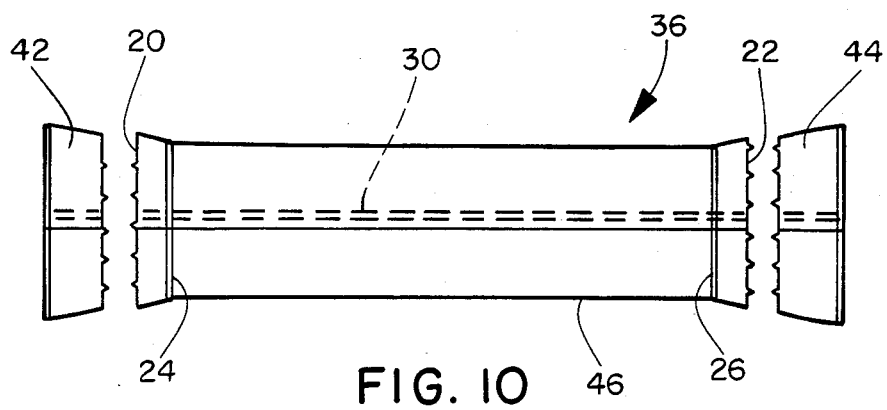
FIG. 10 is a plan view of the package of the invention opened.
Figure 11:
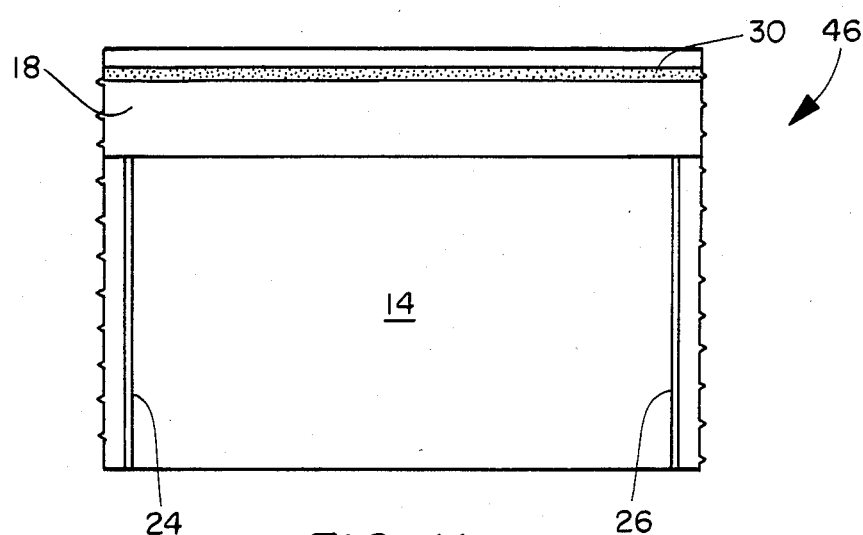
FIG. 11 is a plan view of the container formed after the package is opened.

FIG. 5 illustrates the folded sheet of FIG. 3 after it has been further treated to be ready for formation of a package. The sheet 12 has been provided with perforation lines 20 and 22 that form tear lines. These perforation lines allow tearing of the package sheet on the lines of perforation. Perforation lines extend through the front 14, back 16 and flap 18. Seal lines 24 and 26 form the front 14 and back 16 into a container that is open at 28. The flap 18 has been provided with a strip of pressure-sensitive adhesive 30. Illustrated in FIGS. 8 and 9 is the package 36 formed by wrapping the formed sheet 12 around an article 38. The adhesive 30 is utilized to seal the package in the longitudinal direction while the ends 39 and 40 have been heat sealed to provide sealing of article 38 from atmospheric contact. FIG. 10 illustrates opening the package 36 by tearing the ends 42 and 44 on perforated lines 20 and 22. After removal of the ends, the article may be pushed from one end of the tube or the container 46 may be unrolled by pulling the pressure-sensitive adhesive on flap 18 loose from the back 16 and unrolling the container 46 for removal of the article 38.

Figures 12, 13:
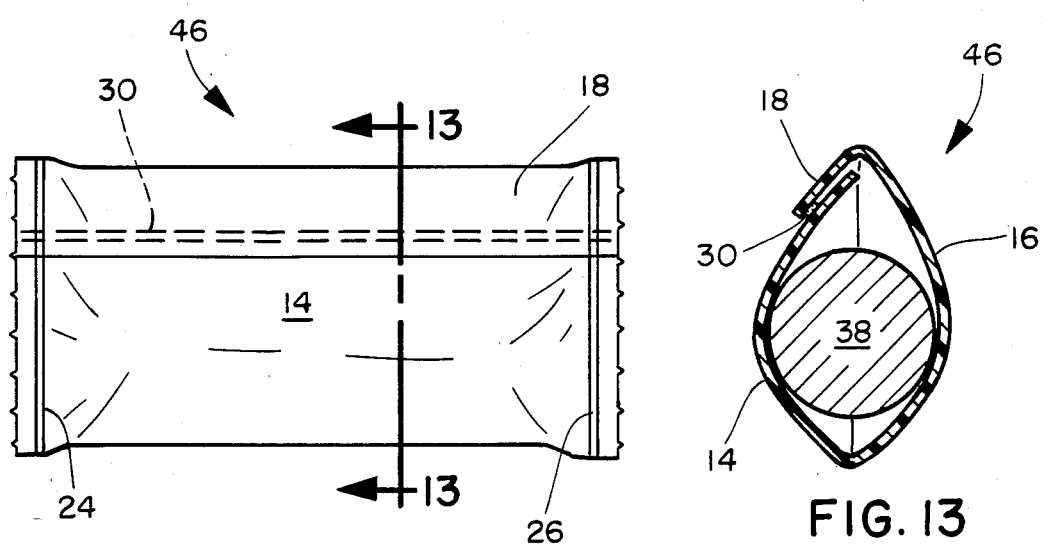
FIG. 12 is a plan view of a container containing a used article.
FIG. 13 is a cross-sectional view along line 13—13 of FIG. 12.

FIGS. 12 and 13 illustrate the container 46 utilized as a disposal device for a used article such as tampon 38. The used article 38 is placed into the envelope container 46 and the flap 18 is sealed with the pressure-sensitive adhesive 30.

Figure 14:
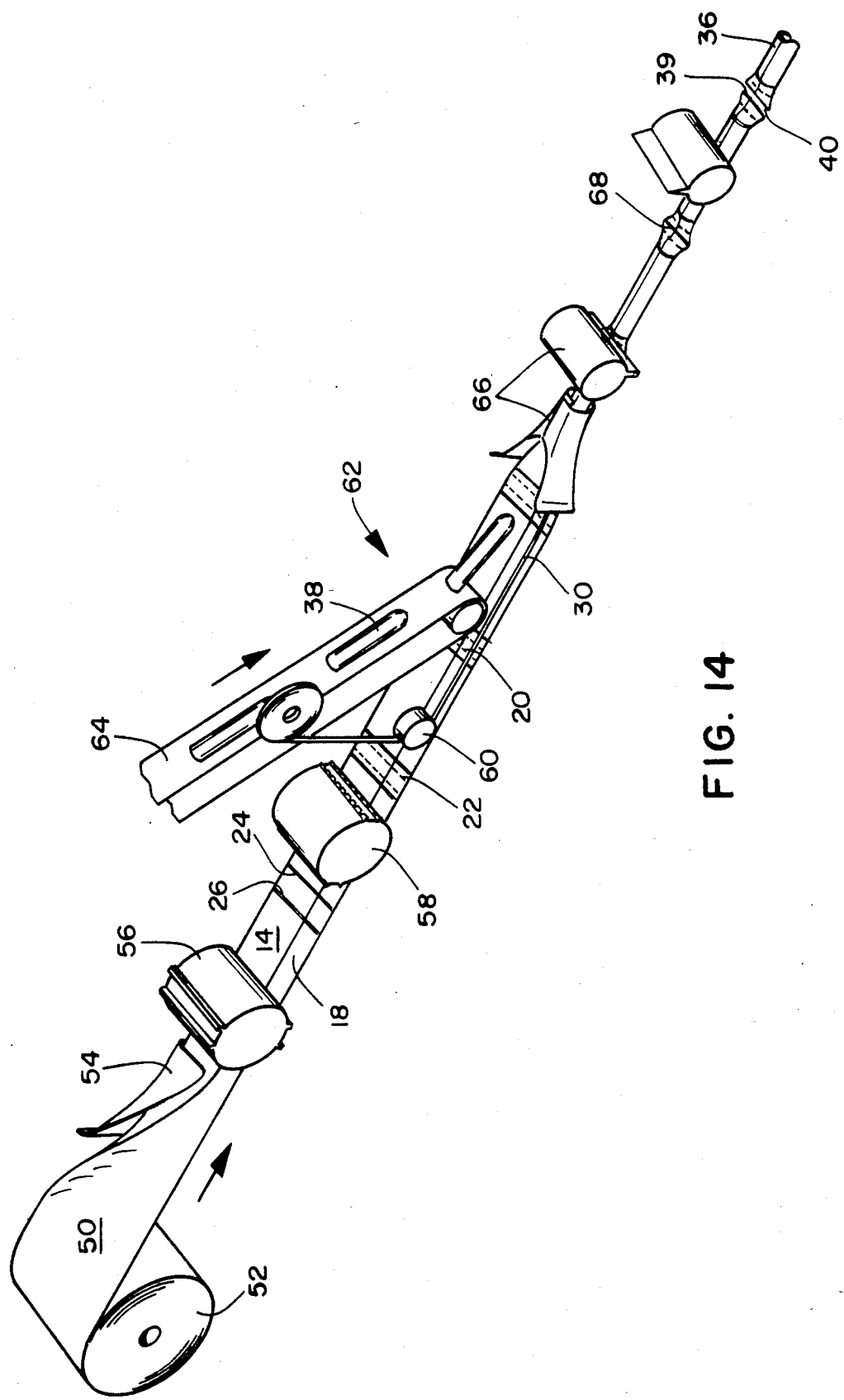
FIG. 14 is a schematic of a process for forming the package of the invention.

FIG. 14 is a schematic illustration of a production process illustrating the low-cost construction techniques that are available for the formation of the instant package and disposal container. The package is formed from a sheet 50 that is provided from a source of sheet material 52. The source of sheet material 50 is fed into a folder 54 where the sheet is folded to form the front 14, back 16 and flap portion 18. The folded sheet is then fed into sealer 56 where the sealing lines 24 and 26 for the sides of the disposal container are applied. The sealed sheet is then fed into perforator 58 where perforation lines 20 and 22 are applied on each side of the container. The folded strip is then fed to the adhesive applicator 60 where pressure-sensitive adhesive 30 is applied to flap 18. The strip is then fed through an article applicator 62 that supplies with the article to be wrapped 38 by conveyor means 64. The article applicator 62 places the article to be wrapped onto the folded strip on the front cover 14. The strip having the article to be packaged resting on the front cover then passes through the wrapper sealer 66 where the strip is wrapped around the article to be packaged and seal lines that seal the ends of the article 39 and 40 and 68 and 69 are applied. The continuous strip of sealed packages then passes into the cutter that cuts the strip into separate packages 36 by cutting between cut lines such as between 39 and 68 and between 40 and 69. This results in sealed separate packages. Instead of cutting, it is possible that the articles could be perforated between the end seal lines 39 and 68 and sold in a strip which would be separated by the user prior to use.

While the invention finds particular benefit in the packaging of feminine napkins and tampons, it is also within the invention to package other materials, particularly those that are undesirable for disposal without being in a somewhat odor-proof and/or concealing container. It is anticipated that the package would be particularly suitable for the sale and disposal of chewing gum, bandages, paint brushes, hospital supplies, diapers and incontinence garments. In all of these areas there is a need for discreet, odor-proof and/or concealed disposal. While the invention has been described with the use of perforations as the means to provide easily opened packages, it is also within the invention to provide tear strips or other means for easy removal of the ends of the package. Further, while the side seals of the disposal container have been set forth with heat sealing to form lines 24 and 26, it is also within the invention to utilize other methods of sealing to form the side seals of the container. Other methods would include the use of adhesives, ultrasonic sealing or sewing.

The package of the invention may be formed from any suitable material. Typical of such materials are paper, metal foils, wax paper, paper-backed foils and the like. A preferred material has been found to be thermoplastic polymer sheets such as polyethylene or polypropylene as this material is easily heat sealed for forming side seals on the container and end seals on the package while additionally allowing easy printing of the package for decoration and instructions and ease of heat sealing.

The method of sealing the flap to the front of the container for disposal, or the the outside of the package for package formation may be any suitable means. Particularly desirable are the pressure-sensitive adhesives such as the known pressure-sensitive synthetic rubber-based styrene-isoprene polymer adhesives. Typical of suitable materials available as a pressure-sensitive adhesive is National 34-2881, a product of National Starch Corporation. Natural rubber-based adhesives also are suitable for the invention. Double-sided tapes are also suitable for use in the sealing of the flap of the invention. A refastenable tape, such as used on diapers, also could be utilized to seal the flap of the container of the invention.

While the package has been described as being particularly desirable for disposal of the article packaged in it after use, it is anticipated that often the container available after the package is opened will be utilized for disposal of the previously used article while the just unwrapped article would be put to use. For instance, when a woman intended to change her tampon she would open a new tampon package, dispose of the used tampon in the container derived from the package, and then put the new tampon to use.

While described with specific embodiments, materials and structure, it is intended that the novel package and disposal system of the invention could be used for a variety of purposes and the invention is intended to be limited only by the scope of the claims attached hereto. For instance, the package could be used to market toys. The container available after the package is open then would be utilized for the storage of the toy. Also, while illustrated with perforated tear strips, the package also could be provided with tear strips or strings.

What is claimed is:

1. A package comprising a front sheet and a back sheet, said back sheet and front sheet being joined at side seals inward of the side edges of the sheets, said front sheet and said back sheet joined together to form a bottom that with said side seals forms a container, said back sheet extending above the top of said front sheet forming a flap, said flap being coated with adhesive and providing areas of weakness forming tear lines generally parallel and outboard of said seals wherein said container is rolled around an object to be packaged such that the adhesive bearing flap is fastened to the exterior of said back sheet and the rolled package has the ends sealed outboard of said tear lines.

2. The package of claim 1 wherein said side seals are formed by application of heat and pressure.

3. The package of claim 1 wherein said package has an article contained within said front sheet.

4. The package of claim 1 wherein said package is opened by tearing along said tear lines and said container is recovered.

5. The package of claim 1 wherein said bottom is a fold joining said back and said front.

6. The package of claim 1 wherein said tear lines are perforated areas.

7. The package of claim 1 wherein said ends are sealed by heat sealing.

8. The package of claim 1 wherein said object comprises a catamenial device and said container comprises a disposal container for said catamenial device.

9. The package of claim 8 wherein said adhesive comprises a pressure sensitive adhesive that also seals said container for disposal.

10. The package of claim 1 wherein said package may be connected to at least one second package by at least one second area of weakness where the package and said at least one second package may be separated.

* * * * *